(12) United States Patent
Natali et al.

(10) Patent No.: US 9,657,565 B2
(45) Date of Patent: May 23, 2017

(54) OPTIMAL SURFACTANT DESIGN FOR RECOVERED HYDROCARBON ENHANCEMENT

(71) Applicant: Halliburton Energy Services, Inc., Houston, TX (US)

(72) Inventors: Sanja Natali, Houston, TX (US); Jason D. Dykstra, Spring, TX (US); Zhijie Sun, Spring, TX (US); Yuzhen Xue, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/889,091

(22) PCT Filed: Dec. 31, 2014

(86) PCT No.: PCT/US2014/072970
§ 371 (c)(1),
(2) Date: Nov. 4, 2015

(87) PCT Pub. No.: WO2016/108879
PCT Pub. Date: Jul. 7, 2016

(65) Prior Publication Data
US 2016/0341037 A1 Nov. 24, 2016

(51) Int. Cl.
*B01D 17/02* (2006.01)
*B01D 17/04* (2006.01)
(Continued)

(52) U.S. Cl.
CPC .............. *E21B 49/08* (2013.01); *B01D 17/02* (2013.01); *B01D 17/047* (2013.01); *C09K 8/58* (2013.01);
(Continued)

(58) Field of Classification Search
CPC ........ B01D 11/04; B01D 21/00; B01D 21/01; B01D 2221/04; B01D 17/02;
(Continued)

(56) References Cited

U.S. PATENT DOCUMENTS 3,288,213 A * 11/1966 King ...................... C09K 8/584
166/270.2
3,630,953 A 12/1971 Whittier et al.
(Continued)

FOREIGN PATENT DOCUMENTS

WO 2013053036 A1 4/2013

OTHER PUBLICATIONS

Publication: Jan Schaerlaekens et al, "Multi-Objective Optimization of the Setup of a Surfactane-Enhanced DNAPL Remediation", Environmental Sci. Technol., published 2005, vol. 39, pp. 2327-2333.*

(Continued)

*Primary Examiner* — Joseph Drodge
(74) *Attorney, Agent, or Firm* — McDermott Will & Emery LLP

(57) ABSTRACT

Methods including the step of producing a bulk fluid from a subterranean formation, the bulk fluid comprising at least water and a hydrocarbon. The bulk fluid is then sampled to form at least one sampled fluid. Next, constituent parameters of the sampled fluid are determined using the hydrophilic-lipophilic deviation (HLD) model. The constituent parameters include the salinity (S) of the sampled fluid, the salinity constant (b); the equivalent alkane carbon number for the hydrocarbon in the sampled fluid (EACN); T is temperature of the sampled fluid; the characteristic curvature for an ionic surfactant composition ($c_c$) or for a nonionic surfactant composition ($c_{cn}$); the surfactant temperature constant for the ionic surfactant composition ($\alpha_T$) or for a nonionic
(Continued)

surfactant composition ($c_T$). Also determining an optimal surfactant or optimal surfactant blend to achieve an oil-water separation morphological phase distribution of the sampled fluid.

16 Claims, 2 Drawing Sheets

(51) Int. Cl.
    *C09K 8/58*     (2006.01)
    *C09K 8/60*     (2006.01)
    *E21B 43/16*     (2006.01)
    *E21B 43/34*     (2006.01)
    *E21B 47/06*     (2012.01)
    *E21B 49/08*     (2006.01)
    *G01N 33/24*     (2006.01)
    *G06Q 10/00*     (2012.01)
    *G06Q 50/00*     (2012.01)
    *E21B 47/00*     (2012.01)
    *G06Q 10/04*     (2012.01)
    *G01N 33/28*     (2006.01)
    *C09K 8/584*     (2006.01)
(52) U.S. Cl.
    CPC .............. *C09K 8/584* (2013.01); *C09K 8/602* (2013.01); *E21B 43/34* (2013.01); *E21B 47/00* (2013.01); *E21B 49/088* (2013.01); *G01N 33/241* (2013.01); *G01N 33/2823* (2013.01); *G06Q 10/04* (2013.01); *G06Q 50/00* (2013.01); *C02F 2209/02* (2013.01); *C02F 2209/05* (2013.01)
(58) Field of Classification Search
    CPC  B01D 17/0208; B01D 17/0214; B01D 17/04; B01D 17/047; C02F 1/00; C02F 1/008; C02F 1/52; C02F 2103/36; C02F 2103/365; C02F 2209/00; C02F 2209/001; C02F 2209/003; C02F 2209/005; C02F 2209/006; C02F 2209/02; C02F 2209/05; C09K 8/00; C09K 8/02; C09K 8/58; C09K 8/584; C09K 8/602; C09K 8/604; E21B 43/16; E21B 43/20; E21B 43/25; E21B 43/26; E21B 43/28; E21B 43/34; E21B 43/38; E21B 47/00; E21B 49/08; E21B 49/081; E21B 49/086; E21B 49/088; E21B 2049/085; E21B 47/06; E21B 49/087; G01N 33/24; G01N 33/241; G01N 33/246; G01N 33/2823; G06F 19/70; G06F 19/702; G06Q 10/04; G06Q 50/00; G06Q 50/02; G06Q 50/04
    USPC .............. 73/152.02, 152.18, 152.42, 152.54; 166/264–267, 305.1, 310, 311; 208/188; 210/634, 639, 708, 739, 749, 800; 700/28–30, 32, 36, 46, 73, 89, 266, 700/271–273; 702/6, 22, 23, 25, 30, 31; 703/2, 6, 9, 10, 12; 705/1.1, 7.11, 7.12, 705/500; 507/200, 203, 935; 585/15, 585/833, 836
See application file for complete search history.

(56) References Cited

U.S. PATENT DOCUMENTS

| | | | | |
|---|---|---|---|---|
| 4,252,192 | A * | 2/1981 | Nussbaum | C09K 8/584 166/270.1 |
| 7,033,504 | B1 | 4/2006 | Blytas et al. | |
| 2008/0047706 | A1* | 2/2008 | Pope | C09K 8/584 166/252.1 |
| 2008/0108527 | A1 | 5/2008 | Varadaraj | |
| 2008/0302531 | A1* | 12/2008 | Berger | C09K 8/584 166/270.1 |
| 2012/0101010 | A1* | 4/2012 | Weerasooriya | C11D 1/06 507/259 |
| 2012/0150519 | A1* | 6/2012 | Bang | E21B 43/16 703/10 |
| 2013/0096036 | A1 | 4/2013 | Quintero et al. | |
| 2014/0317999 | A1* | 10/2014 | Weerasooriya | C09K 8/86 44/301 |

OTHER PUBLICATIONS

Publication: Luis E. Zerba, "An optimization methodology of alkaline-surfactant-polymer flooding processed using field scale numerical simulation and multiple surrogates", Journal of Petroleum Science and Engineering, published 2005, vol. 47, pp. 197-208.*
AbbottApps Production, Measure EACN, http://www.stevenabbott.co.uk/PracticalSurfactants/MeasureEACN.html.
AbbottApps Production, Measurements, http://www.stevenabbott.co.uk/PracticalSurfactants/Measurements.html.
International Search Report and Written Opinion for PCT/US2014/072970 dated Sep. 21, 2015.

* cited by examiner

OPTIMAL SURFACTANT DESIGN FOR RECOVERED HYDROCARBON ENHANCEMENT

BACKGROUND

The present disclosure generally relates to subterranean formation operations and, more particularly, optimal surfactant design for recovered hydrocarbon enhancement.

The production of underground hydrocarbons often requires substantial investment in drilling and pumping equipment. When production is underway, up-front costs can be recouped provided that operating costs remain low enough for the sale of oil and/or gas to be profitable. During the production of hydrocarbons, relatively large quantities of water may be produced along with the hydrocarbons (also referred to herein simply as "oil"). In some formations, water and other by-products can amount to as much as eighty to ninety percent of the total production yield. The presence of water comingled with produced oil is a significant factor affecting the cost of many subterranean formation operations. Many profitable formations may become uneconomic because of excessive water production. Costs involved with pumping, separating, collecting, treating and/or disposing of water often have a devastating impact on profit margins, particularly for older wells with declining hydrocarbon production.

Separating the oil from the water in a produced fluid enables operators to recover pure or substantially pure oil and/or reuse, recondition, or otherwise process the water. Such separation may allow an operator to reduce transportation and disposal costs, to maintain the separated water in the formation or at the surface at a well site (e.g., at an offshore location), and the like. In some instances, produced water separated from produced oil may be suitable for agriculture, livestock, and/or wildlife use, potentially creating a means of beneficially recycling the separated water and/or a revenue stream.

Various methods have been employed for separating water from produced oil. For example, oil and water are typically pumped or otherwise flowed together to the surface where they are treated by heat to separate the oil from the water. The heat separates the denser water from the less-dense oil. In other instances, the oil and water may be separated using a hydroclone, which spins the produced fluid (e.g., the oil and water mixture returned from the subterranean formation) and use acceleration to separate the oil and water. These separation techniques may also be used in combination with downhole equipment (e.g., submersible pumps) to achieve separation of oil and water produced by a formation at a downhole location.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
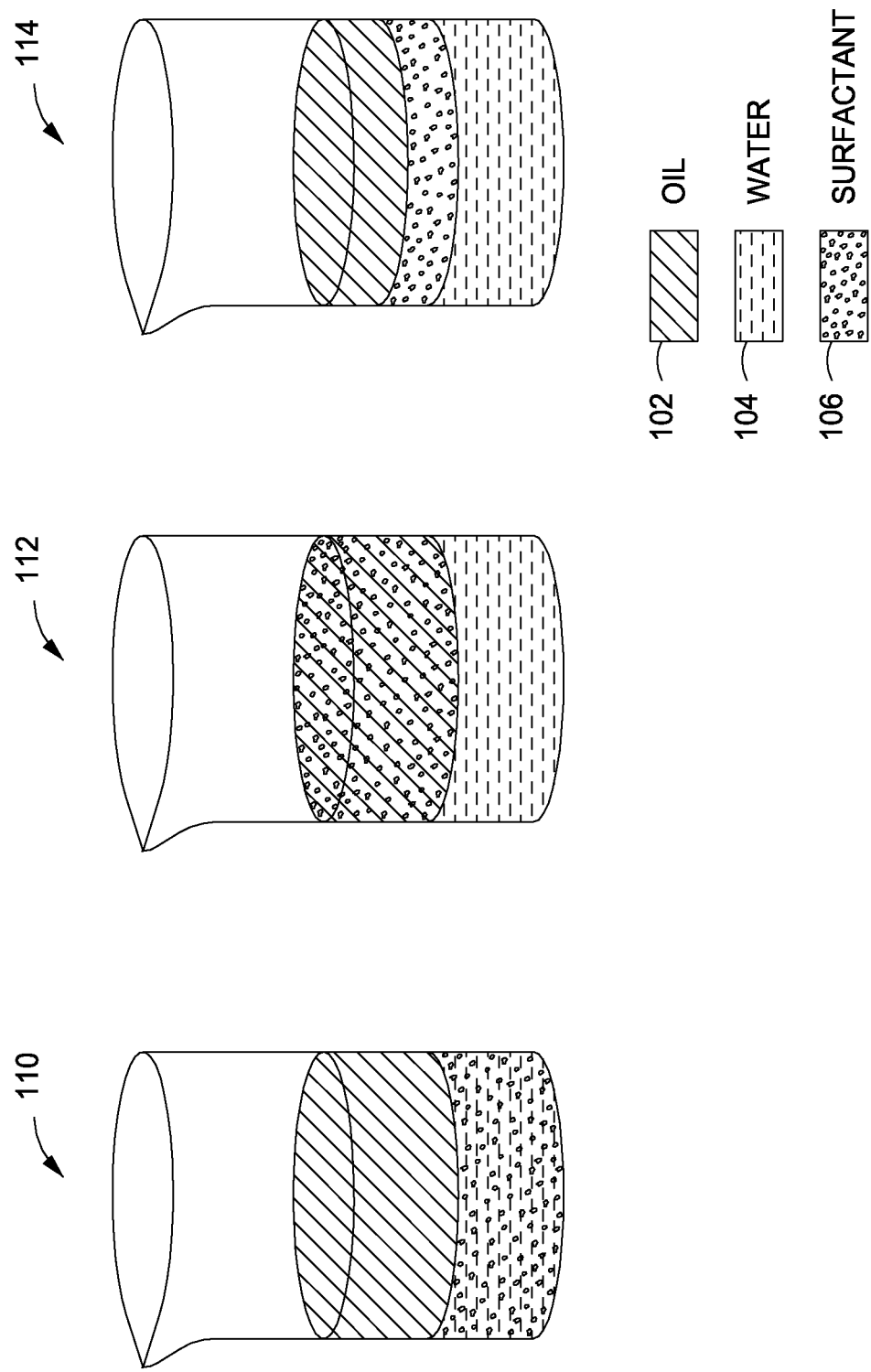
FIG. 1 provides an illustration of the morphological phases of an oil-water system with added surfactant.

The present disclosure generally relates to subterranean formation operations and, more particularly, optimal surfactant design for recovered hydrocarbon enhancement. More specifically, the methods of the present disclosure take into account various practical considerations in selecting surfactants for use in recovered hydrocarbon enhancement, including the action of the surfactant to adequately break emulsions of oil and water to enable separation thereof. The practical considerations, thus, permit operators to select suitable surfactants while also reducing material costs, supply chain costs, and other associated costs. The methods herein also may result in use of blended surfactants that exhibit increased efficacy, while reducing the costs previously listed, and described in greater detail below.

As used herein, the term "optimal surfactant" refers to a surfactant that forms an oil-water separation morphological phase distribution with produced fluid from a subterranean formation, while accounting and balancing for experimental costs, material and supply chain costs, uncertainty of the surfactant, and robustness of the surfactant. The optimal surfactant(s) designed using the methods described herein may be introduced into a produced fluid from a subterranean formation at a surface location to achieve separation of the oil and water therein. As used herein, the term "subterranean formation," or simply "formation," refers to any material under the surface of the earth, encompassing both areas below exposed earth and areas below earth covered by water (e.g., ocean water or fresh water). A wellbore may be any opening in a subterranean formation, such as an opening for recovering produced hydrocarbons, or produced hydrocarbons comingled with water.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques. As used herein, the term "about" with reference to numerical quantities may mean ±5% of a stated numerical value, encompassing any value and subset therebetween.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill the art and having benefit of this disclosure.

While compositions and methods are described herein in terms of "comprising" various components or steps, the compositions and methods can also "consist essentially of" or "consist of" the various components and steps.

The optimal surfactant design system and methods of the present disclosure use, in part, the hydrophilic-lipophilic deviation ("HLD") model to achieve fluid separation of oil and water produced from a formation. The HLD model quantifies the relative impact of the hydrophilic-lipophilic nature of oils and surfactants on the morphological phase behavior a fluid comprising oil, water, and surfactant. Because produced fluids comprise oil and water naturally, the optimal surfactant design system and methods herein are used to determine the amount and type of surfactant to include in the produced fluids to achieve the desired morphological phase, while taking into account practical considerations, such as costs.

As shown in FIG. 1, three (3) morphological phases may exist when a surfactant 106 is added to a fluid comprising comingled oil 102 and water 104 (an "oil-water fluid"), each associated with a relative HLD value, discussed in detail below. As used herein, the term "oil-water-surfactant system," (or "O/W/S system"), may be used to describe an oil-water system having a surfactant added therein. The morphological phases include an oil-in-water morphological phase 110, a water-in-oil morphological phase 112, and an oil-water separation morphological phase 114. The oil-in-water morphological phase 110, also referred to as a "Winsor Type I" emulsion (including micro- and nano-emulsions) is characterized by an water 104 and surfactant 106 emulsion, leaving an excess oil 102 phase. The water-in-oil morphological phase 112, also referred to as a "Winsor Type II" emulsion (including micro- and nano-emulsions) is characterized by an oil 102 and surfactant 106 emulsion, leaving an excess water 104 phase. Finally, the oil-water separation morphological phase 114, also referred to as a "Winsor Type III" emulsion (including micro- and nano-emulsions), is characterized by a three-phase separation in which the surfactant 106 is located at the face between the oil 102 and water 104. It will be appreciated by one of skill in the art that some intermixing between the surfactant 106, the oil 102, and the water 104 occurs at each morphological phase type. For example, in the oil-water separation morphological phase, some intermixing between the surfactant 106 and the oil 102 and water 104 may occur at the face therebetween.

To achieve optimal separation of the water 104 from the oil 102 in an oil-water system by including a surfactant therein, accordingly, the desired morphological phase is the oil-water separation morphological phase 114. In such a phase, the oil 102, the water 104, and the surfactant 106 may be easily separated by relatively simple means, such as by classical separation methods. Other physical separation methods may also be employed, without departing from the scope of the present disclosure. Achieving the oil-water separation morphological phase 114 may be dependent on the type of surfactant selected, the type of oil in the oil-water system, the salinity of the water 104 in the oil-water system, the temperature of the in the O/W/S system, and the like, as described in detail below.

The HLD model is used in the present disclosure as a formulating tool for achieving an oil-water separation morphological phase; it is also used to determine the constituent contents of a produced fluid that are represented in the HLD model. The HLD of an O/W/S system is dependent on the type and amount of surfactant used to form the desired oil-water separation morphological phase 114 (FIG. 1). For ionic surfactants, the HLD may be calculated using Equation 1, below; for nonionic surfactants, the HLD may be calculated using Equation 2, below:

$$HLD=ln(S)-k*EACN+c_c-\alpha_T(T-25°\ C.)+f(A) \quad \text{Equation 1,}$$

$$HLD=b(S)-k*EACN+c_{cn}-c_T(T-25°\ C.)+f(A) \quad \text{Equation 2,}$$

where S is the salinity of the water of the an O/W/S system (in g/100 mL water), with log dependency in Equation 1; b is a salinity constant equivalent for nonionic surfactants (unitless); EACN is the equivalent alkane carbon number for the oil of the O/W/S system (unitless), which reflects the oil hydrophobicity based on the number of carbons in the oil or the equivalent number of carbons; T is temperature (in ° C.) of the O/W/S system at the point where the surfactant is to be added to the oil-water system; $f(A)$ is a function of alcohol (or co-solvent) type and concentration in the O/W/S system (unitless value); k is a surfactant constant, which depends on the type of surfactant head group (unitless); $c_c$ is the characteristic curvature (i.e., surfactant hydrophilic-lipophilic nature) for an ionic surfactant (unitless value); $c_{cn}$ is the characteristic curvature (i.e., surfactant hydrophilic-lipophilic nature) for a nonionic surfactant (unitless value), which reflects the nonionic surfactant hydrophobicity; $\alpha_T$ is a surfactant temperature constant for ionic surfactants (1/° C.), which reflects the ionic surfactant hydrophobicity; and $c_T$ is a surfactant temperature constant for nonionic surfactants (1/° C.). Each of b, k, $\alpha_T$, and $c_T$ are constants of fixed value depending on the particular type of surfactant.

Accordingly, the HLD model takes into consideration salinity, temperature, alcohol content, and characteristics of the hydrophobicity and type of oil and surfactant (i.e., "HLD parameters"). As an example, as the EACH value increases, the HLD decreases. Additionally, the surfactant temperature constants may be positive or negative; thus, for example, the ionic surfactant temperature constant may be about 0.01, such that as the temperature, T, increases above the reference value of 25° C., the HLD decreases. On the other hand, for example, the nonionic surfactant temperature constant of an ethoxylate surfactant may be about −0.06, such that as the temperature, T, increases above the reference value of 25° C., the HLD increases. Also, as the characteristic curvature of the ionic surfactant, $c_c$, or the nonionic surfactant, $c_{cn}$, increases, the HLD also increases.

The HLD value produced by Equation 1 or Equation 2, depending on the type of surfactant used, predicts the morphological phase of a water-oil system. Referring again to FIG. 1, when the HLD value is equal to zero (0), the oil-water separation morphological phase 114 is achieved and represents perfect separation of the oil 102 and water 104 phases. As the HLD decreases to values less than zero (0), a water-oil system comprising a surfactant will adopt the oil-in-water morphological phase 110; whereas as the HLD increases to values greater than zero (0), the water-oil system comprising a surfactant will adopt the water-in-oil morphological phase 112. Thus, to achieve perfect oil-water separation morphological phase 114, the HLD should be equal to zero (0). A perfect oil-water separation morphological phase 114 may be characterized as having no surfactant 106 molecules in either the oil 102 phase or the water 104 phase. However, in some less-perfect oil-water separation morphological phases 114, the oil 102 and water 104 may be separated from one another sufficient to separate the water 104 from the oil 102 in produced fluids, but the surfactant 106 molecules may seep into the water 104 or oil 102 phases past the interfaces thereof. Also of note, while the figure shows perfect separation, in practice it is expected that at least some of the oil may appear in the water phase and vice-versa. Because the optimal surfactant design system and methods described herein are concerned with practical considerations (e.g., costs), as well as achieving oil-water separation morphological phase distribution of produced fluids, the embodiments herein do not require a perfect oil-water separation morphological phase distribution. However, it is generally desirable to have any imperfections occur in the middle phase—that is, some additional amounts of the oil and/or water may be present in the surfactant layer, but the goal is to have the oil and water layers as pure as possible. Accordingly, although in some embodiments HLD may ideally=0, in other embodiments, the HLD may still be acceptable where the HLD ranges from +/−1, preferably +/−0.5, more preferably +/−0.3, encompassing any value and subset therebetween. By way of example a system of water, SDHS (sodium dihexylsulfosuccinate), and toluene may be considered acceptable if the system achieves an HLD −0.2 to 0.3.

Using the HLD model in Equation 1 and 2, as described above, b, k, $\alpha_T$, $c_T$, $c_n$, and $c_{cn}$ are related to the type of surfactant, and S, EACN, and T are related to properties of the produced fluid (i.e., the fluid produced and recovered at the surface from a subterranean formation). Referring first to the properties of the produced fluids, such properties may be determined experimentally or from field tests. In some embodiments, it may be preferred to determine first the EACN of the produced fluids, thereby enabling back calculation of certain variables related to a surfactant (e.g., the characteristic curvature) that may produce an oil-water separation morphological phase distribution, as described below. Other means of determining the produced fluid properties in the HLD model may also be employed, without departing from the scope of the present disclosure.

Below, examples of determining HLD according to the present disclosure are provided with reference to first determining an unknown EACN value for a specific type of oil. However, it will be appreciated that these examples are not limiting, and any parameter, and in any combination, in the HLD model may be used to determine the type and amount of surfactant(s) necessary to achieve the oil-water separation morphological phase 114 previously discussed. That is, any one, more than one, or all of the salinity, temperature, characteristics of the hydrophobicity and type of oil and surfactant, and the alcohol content where applicable may be used to determine the type and amount of surfactant(s) necessary to achieve the oil-water separation morphological phase 114, without departing from the scope of the present disclosure. Moreover, the methods described with reference to the determining the EACN value (e.g., adding known surfactant, adding known salt, adding known oil, and the like) may be employed to determine any other HLD parameter in the HLD model, without departing from the scope of the present disclosure.

The EACN value is specific for each type of oil, and explains the hydrophobicity of the oil. The EACN for alkane oils may be equivalent to the number of carbons atoms in the oil molecule. However, for other oil types, the number of carbon atoms alone may not predict the EACN of the oil, or the oil's hydrophobicity. The EACN of an oil may be determined experimentally where the HLD value is set to equal zero (0), by using known values for the remaining variables in either Equation 1 (ionic surfactant) or Equation 2 (nonionic surfactant). The temperature variable, T, may be controlled at temperature 25° C., such that the variable is effectively no longer taken into account in determining the EACN value, or may be determined experimentally. Similarly, the salinity, S, may be effectively removed as a variable for determining HLD by using a known salinity and measuring the salinity using known techniques (e.g., a conductivity meter, a refractometer, a hydrometer, and the like).

In one instance, the EACN may be determined by using at least two known surfactants having a characteristic curvature and a known salinity based on the relative combination of the known surfactants ("surfactant-surfactant method"). In some instances, use of a two or more of known ionic surfactants in varying concentrations and proportions to one another may cover a wider range of curvature values, which may be preferred to experimentally determining the EACN of a particular O/W/S system. The selected known surfactants should preferably not include surfactants that form complex phases between each other, should preferably be relatively compatible with oil-water systems generally produced from formations, and the like. The characteristic curvature of a mixture of surfactants is determined based on a linear relationship of the added surfactant types, based on Equation 3 for ionic surfactants, and Equation 4 for nonionic surfactants, as follows:

$$C_{c\text{-}mix} = \Sigma_i y_i C_{c_i} \qquad \text{Equation 3,}$$

$$C_{cn\text{-}mix} = \Sigma_i y_i C_{cn_i} \qquad \text{Equation 4,}$$

where $y_i$ is the fraction of the $i^{th}$ surfactant component (unitless value) (e.g., 0.25 if that surfactant component makes up 25% of the surfactant composition); $C_{c_i}$ is the characteristic curvature of the $i^{th}$ ionic surfactant component; and $C_{cn_i}$ is the characteristic curvature of the $i^{th}$ nonionic surfactant component.

In another instance, the EACN may be determined using at least one known surfactant (e.g., known characteristic curvature) and at least one known oil component (e.g., known EACN), to be included in the O/W/S system in addition to the already present oil component ("surfactant-oil method"), each in varying concentrations and proportions to one another. The chosen known oil component(s) should not contribute to forming an oil-water separation morphological phase. The ratios of the different oils may be adjusted until the HLD value=0, and the EACN of the known and unknown oil mixture is elucidated. Thereafter, the EACN of the unknown oil may be calculated. The EACN value of a mixture of oils is determined based on a linear relationship of the added oil types, based on Equation 5, as follows:

$$EACN_{mix} = \Sigma_i x_i EACN_i \qquad \text{Equation 5,}$$

where $x_i$ is the fraction of the $i^{th}$ oil component (e.g., the unknown oil component) (unitless value); and $EACN_i$ is the EACN of the $i^{th}$ oil component (e.g., the unknown oil component).

The EACN of an unknown oil in an O/W/S system may additionally be determined using the HLD model described herein using a known surfactant (e.g., known characteristic curvature) and a known range of salinities (e.g., range of salinity concentrations), S, such as by adding a salt to the O/W/S system or by diluting the O/W/S system with water ("salinity method"). Use of an ionic surfactant, in such instances, may permit a greater range of salinities to be evaluated, but it may be necessary to also take into account the salinity of the ionic surfactant itself. In some embodiments, it may be preferred to select a surfactant that can withstand very high salinities to more accurately determine the EACN of the unknown oil.

In practice, each of the above methods, the surfactant-surfactant method, the surfactant-oil method, and the salinity method, a variety of concentrations and/or types of the known parameters may be included in a series of identical O/W/S systems, so as to enhance the ability to accurately determine the EACN of the particular system. That is, an O/W/S/system (e.g., the produced fluids comprising surfactant) may be aliquoted by any means suitable into two or more testing tubes and the parameters are varied until the formation of an oil-water separation morphological phase occurs in at least one of the testing tubes.

Once the EACN of an unknown oil in an O/W/S system is known, other unknown parameters may be calculated based on the know parameters and known EACN, thereby enabling determination of the surfactant characteristics detailed in the HLD model for achieving HLD=0 (or substantially 0). As used herein, the term "substantially" means largely, but not necessarily wholly. As previously discussed, determination of one or more other unknown parameters may be utilized based on the methods described herein, without departing from the scope of the present disclosure. Accordingly, with the known surfactant qualities required, a surfactant and dosage of the surfactant may be selected to achieve oil-water separation morphological phase distribution desired for the oil-water system originally tested (i.e., the produced fluid). Moreover, a combination of surfactants may also be employed. Such surfactants may be commercially available, laboratory made, or a mixture of one or both to achieve the desired qualities of oil-water separation.

However, selection of a surfactant according to the system and methods described herein, as mentioned previously, is not solely dependent on the ability of the surfactant to form a perfect oil-water separation morphological phase distribution. Rather, other factors are relevant in selecting the surfactant or blend of surfactants including, but not limited to, the costs associated with the surfactant, including costs, experimental costs, and the like, health, safety, and environmental concerns (HSE), the uncertainty of the surfactant, the robustness of the surfactant, and the like. As used herein, the term "costs", thereof refers to material costs and supply chain costs, measured in monetary units (e.g., USD, and the like). As used herein, the term "material costs" refer to the assets needed to purchase suitable surfactants, measured in monetary units (e.g., USD, and the like). As used herein, the term "supply chain costs" refers to transportation costs of surfactant chemicals and containers, measured in monetary units (e.g., USD, and the like).

As used herein, the term "uncertainty," and grammatical variants thereof refers to "a non-negative parameter characterizing the dispersion of the values attributed to a measured quantity or a quantity derived from at least one measured quantity." As used herein, the term "experimental costs" refers to the cost of performing experimental work (including the time costs, equipment costs, supply costs, etc.) to determine the properties of surfactants, e.g., characteristic curve. As used herein, the term "HSE" refers to "Health, Safety, and Environmental" and is meant to provide a metric for determining the potential impact of the optimized surfactant blend, wherein the optimal value is zero and the surfactant has no negative impact on Health Safety and Environmental. By way of example, the HSE impact of a surfactant may be based on the National Fire Protection Association ("NFPA") diamond safety placards that include space for three numerical designations of safety (health, flammability, and instability) rated from 0-4, with zero representing a "no hazard" and 4 representing the highest risk. In addition, the NFPA diamond safety placards include a fourth space for an indication of "special hazards. Using that rating system and considering the special hazard section as either a 1 (special hazard indicated) or a zero (no special hazard indicated), then the user may add the indications from the diamond, yielding a maximum hazard of thirteen (4+4+4+1) and a minimum hazard of zero. One of skill in the art will recognize that this is merely one method of determining HSE risk and other methods may be applicable.

As used herein, the term "robustness" refers to the sensitivity of a surfactant or blended surfactant to the surrounding environment (e.g., a downhole location). That is, the term refers to whether the surfactant is able to maintain steady HLD in the circumstance of changing salinity then the system is very robust and the number would be low, with zero being a perfectly robust surfactant. By example, if you have a system of water, SDHS (sodium dihexylsulfosuccinate), and toluene wherein the salinity changes from 1.1% to 3.5% and that causes the HLD to change from −0.79 to 0.36 the robustness number would be calculated using the change in HLD divided by the change in salinity [((|−0.79|+|0.36|)/2.4)=0.479] and the robustness used for the system would be 0.479 1/%. One of skill in the art will recognize that the surfactant may, in fact, be insensitive to changes in salinity but may be sensitive to temperature; thus, robustness may be used to determine the sensitivity of the surfactant in the system with respect to any of the HLD parameters.

In some embodiments, the surfactants may be optimized by blending one or more surfactants to maximize on favorable qualities, while minimizing unfavorable qualities. The surfactant or blended surfactant(s) optimized according to the methods described herein using Equation 6, below:

$$W_1 \cdot HLD^2 + W_2(\rho-\bar{\rho})^2 + W_3(\mu-\bar{\mu})^2 + W_4 \cdot cost + W_5 \cdot uncertainty + W_6 \cdot HSE + W_7 \cdot experiment\_cost + W_8 \cdot robustness \quad \text{Equation 6,}$$

where W is a user defined weighting factor for each, $\rho$ is the density of the surfactant, and $\mu$ is the viscosity of the surfactant. In some instances, wherein the surfactant is a blend of multiple surfactants, $\rho = f_\rho(c_i, \rho_i)$, i=1, 2, ..., N, and $\mu = f_\mu(c_i, \mu_i)$, i=1, 2, ..., N, where $c_i$ is the percentage of the composition of the $i^{th}$ surfactant in the blended surfactant composition. For example, if the selected surfactant blend uses two surfactants, one at 25% and one at 75% of the blend, then c1 would be 0.25 and c2 would be 0.75. The equation above may be moved in an effort to minimize the uncertainty or to create an optimized system wherein the uncertainty may be somewhat higher than minimum but within a level of acceptable risk. Also, depending on the needs of the specific job, it may be desirable to place the W weighting factor to zero for elements that are deemed less critical for the specific job being undertaken. By way of example, if close adherence to HLD=0 is critical but the time and expense associated with experiment cost is not, it may be desirable to set $W_7$ at zero and to set $W_1$ at an arbitrarily high number. The $W_1$ would need to be high is such a situation to weight that factor more heavily and it account for the fact that HLD is generally a very small number. Also of note is the fact that the equation should be determine such that the additive result is unitless. Thus, for example, if it is expected that the density and viscosity calculations will be close to that of water, and no special weight is to be given to those factors, it may be desirable to set $W_2$ to 1×10−6 m6/kg2 (the inverse of the density of water) and $W_3$ to 1×10−6 ($m^2s^2/kg^2$) (the inverse of the viscosity of water)

Each of the HLD, cost, uncertainty, HSE, experimental_cost, and robustness variables may be determined according to Equations 7 through 13 below. Each of the Where variables are repeated in each Equation, their meaning is not altered and they will, therefore, not be discussed in duplication:

$$HLD = S\sum_{i=1}^{N} c_i \cdot b_i(S) - EACN \sum_{i=1}^{N} c_i \cdot k_i + \sum_{i=1}^{N} c_i \cdot c_{c,i} + (T - 25^\circ \text{ C.}) \sum_{i=1}^{N} c_i \cdot \alpha_{T,i} + f(A),$$ Equation 7 where Equation 7 is directed toward ionic surfactants and comprises the same variables as listed in Equation 1, and where $c_i$ is the composition of the $i^{th}$ surfactant in a blended surfactant composition, Equation 7 above is for nonionic surfactants, for ionic surfactants the term $b_i(S)$ is substituted by $\ln(S_i)$, similar to Equations 1 and 2 above;

$$HLD = S\sum_{i=1}^{N} c_i \cdot b_i - EACN \sum_{i=1}^{N} c_i \cdot k_i + \sum_{i=1}^{N} c_i \cdot c_{cn,i} + (T - 25^\circ \text{ C.}) \sum_{i=1}^{N} c_i \cdot c_{T,i} + f(A),$$ Equation 8 where Equation 8 is directed toward ionic surfactants and comprises the same variables as listed in Equation 2;

$$\text{cost} = \sum_{i=1}^{N} c_i \cdot (\text{cost}_{m,i} + \text{cost}_{s,i}),$$ Equation 9 where $\text{cost}_{m,i}$ is the material cost of the surfactant or the $i^{th}$ surfactant in a blended surfactant and $\text{cost}_{s,i}$ is the supply chain cost of the surfactant or the $i^{th}$ surfactant in a blended surfactant;

$$\text{uncertainty} = \sum_{i=1}^{N} f_{un}(c_i, \text{uncertainty}_i),$$ Equation 10 where $f_{un}$ is a function of the uncertainty of the surfactant or of the $i^{th}$ surfactant in a blended surfactant, based on the composition of the surfactant or the $i^{th}$ surfactant in a blended surfactant, $c_i$, and the uncertainty thereof, uncertainty$_i$;

$$HSE = \sum_{i=1}^{N} f_{HSE}(c_i, HSE_i),$$ Equation 11 where $f$ is a function of the HSE of the surfactant or of the $i^{th}$ surfactant in a blended surfactant, based on the composition of the surfactant or the $i^{th}$ surfactant in a blended surfactant, $c_i$, and on the HSE thereof, $HSE_i$;

$$\text{experiment\_cost} = \sum_{i=1}^{N} f_{exp}(c_i, \text{uncertainty}_i),$$ Equation 12 where $f_{exp}$ is a function of the experimental cost of the surfactant or of the $i^{th}$ surfactant in a blended surfactant, based on the composition of the surfactant or the $i^{th}$ surfactant in a blended surfactant, $c_i$, and the uncertainty thereof, uncertainty$_i$. The experimental cost is characterized by $c_i$ and uncertainty$_i$ because usually a reduced uncertainty leads to a higher experimental cost because in order to increase the certainty of performance generally additional experiments must be performed. That is, if no experiments are performed, there is no experimental cost and $c_i=0$;

$$\text{robustness} = \sum_{i=1}^{N} f_{rb}(c_i, \text{uncertainty}_i, T, \sigma_T),$$ Equation 13 where $f_{rb}$ is a function of the robustness of the surfactant or of the $i^{th}$ surfactant in a blended surfactant, based on the composition of the surfactant or the $i^{th}$ surfactant in a blended surfactant, $c_i$, the uncertainty of the surfactant or the $i^{th}$ surfactant in a blended surfactant, uncertainty$_i$, temperature, T, and the temperature standard deviation, $\sigma_T$, thereof. For example, when more uncertainty (or, equivalently, less accuracy) is acceptable, the operator may not have continue to experiment until HLD=0 and may, instead, reach a level of imperfect but acceptable separation of oil and water. Minimization of robustness in Equation 6 may allow the selection of surfactants or blended surfactants with smaller surfactant temperature constants, $\alpha_T$ or $C_T$. Temperature is often one of the key factors affecting HLD in downhole performance. This may be because other factors, such as salinity, do not tend to change drastically as part of a treatment. By contrast, downhole temperature can be easily, and sometimes drastically, affected by wellbore treatments. Thus, where a more robust HLD is desired, it is important to select surfactants that yield an HLD less sensitive to temperature (i.e., smaller temperature constants are more favorable). The temperature standard deviation ($\sigma_T$) goes to the range of temperatures expected to be encountered. This variable can be either estimated or learned from previous job data from the same or a similar well. Knowing the standard deviation allows for better characterization of the robustness. For example, an operator may be able to select an inexpensive, readily available surfactant even though that surfactant is sensitive to temperature if the operator knows that the temperature standard deviation is small.

Referring to Equations 7 and 8, each of b, k, $\alpha_T$, and $c_T$ are constants of fixed value depending on the particular type of surfactant and may be determined with known experimental techniques. Each of the surfactant constants may have its own uncertainty for use in Equation 10, 12, and/or 13. When two or more surfactants are blended together, the surfactant variables, b, k, $\alpha_T$, $C_T$, $c_n$, and $c_{cn}$, in Equations 7 and 8 are approximated by the linear combination of the corresponding variables for each surfactant included in the blended surfactant.

Referring to Equation 9, material cost, $\text{cost}_{m,i}$, is a fixed cost related to the cost of the surfactant itself, including the volume of surfactant required to form the oil-water separation morphological phase distribution required, and the like. However, the supply chain cost, $\text{cost}_{s,i}$, is variable because if a particular surfactant is not used, no supply chain cost will exist (e.g., $\text{cost}_{s,i}=0$ if $c_i=0$, and $\text{cost}_{s,i}>0$ if $c_i>0$). That is, in some circumstances the operator selects and must pay for the surfactant whereas in other cases a customer may specify the surfactant and pay directly for the material costs and the operator only determines the amount used rather than the particular surfactant. In some embodiments, the supply chain cost may be calculated using Equation 14, below:

$$\text{cost}_{s,i} = \text{cost}_{per\ sack} * n_{sack,i} \qquad \text{Equation 14,}$$

where $\text{cost}_{per\ sack}$ is the material cost by the sack, $n_{sack,i}$ is the number of sacks of the $i^{th}$ surfactant in a blended surfactant, $m_{per\ sack}$ is the mass of the surfactant per sack, $m_{total}$ is the total mass of the surfactant or blended surfactant.

In some embodiments, rather than using the uncertainty Equation 10, Equation 15 may be used for ionic surfactants or Equation 16 may be used for nonionic surfactants:

$$\text{uncertainty}_{ionic} = S^2 \sum_{i=1}^{N} c_i^2 \cdot \sigma_{b_i} + EACN^2 \sum_{i=1}^{N} c_i^2 \cdot \sigma_{k_i} + \qquad \text{Equation 15}$$

$$\sum_{i=1}^{N} c_i^2 \cdot \sigma_{c,i} + (T - 25^\circ\ C.)^2 \sum_{i=1}^{N} c_i^2 \cdot \sigma_{\alpha_T,i},$$

$$\text{uncertainty}_{nonionic} = S^2 \sum_{i=1}^{N} c_i^2 \cdot \sigma_{b_i} + EACN^2 \sum_{i=1}^{N} c_i^2 \cdot \sigma_{k_i} + \qquad \text{Equation 16}$$

$$\sum_{i=1}^{N} c_i^2 \cdot \sigma_{cn,i} + (T - 25^\circ\ C.)^2 \sum_{i=1}^{N} c_i^2 \cdot \sigma_{c_T,i},$$

Whereas Equation 10, above is a general equation, equations 15 and 16 take into account the standard deviation ($\sigma$) of the various surfactant properties in the HLD model, as well as other parameters in the HLD model, which may be preferred if when the range of parameter variation is small, or when the uncertainty is a linear combination of all factors affecting HLD, (because Equation 15 and 16 is linear) Where an ionic surfactant is being considered, the term $\sigma_{b_i}$ should be substituted with the term $\sigma_{ln(S)}$.

Figure 2:
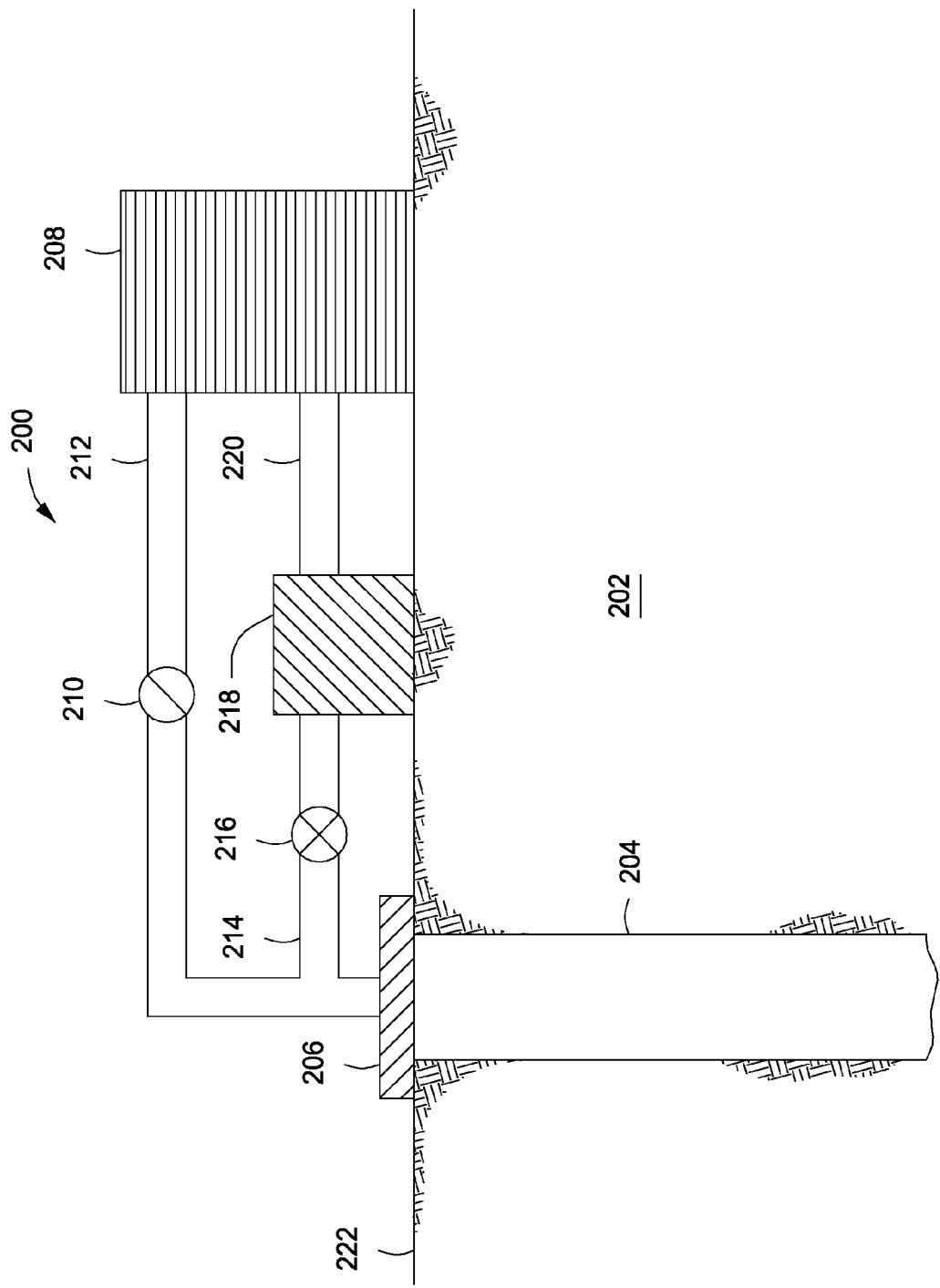
FIG. 2 provides an illustration of a production system suitable for use in conjunction with the methods described herein.

Referring now to FIG. 2, illustrated is a production system 200 for producing fluids from a subterranean formation 202. The production system 200 includes a wellbore 204 penetrating the subterranean formation 202 with a wellhead 206 where the produced bulk fluid exits the wellbore 404 (which may be cased or uncased) to the surface 222. The produced fluid may then be conveyed to a storage container 208 (e.g., a tank or a tanker truck) or a pipeline (not illustrated) via a main tubular 212 with a pump 210 (if needed). As illustrated, in some embodiments, the produced fluids from the subterranean formation 202 may be sampled using a sampling tubular 214 (e.g., a tube, a hose, and the like). The sampling tubular 214 may be in fluid communication with the main tubular 212 and a valve 216 may be arranged on the sampling tubular 216 to have an open or closed position. When the valve 216 is in the open position, produced fluid may flow through the sampling tubular 216 and into a sample chamber 218, where samples of the produced fluid may be taken for use in designing an optimal surfactant, as described herein. In some embodiments, the sample chamber 218 may additionally be in fluid contact with the storage container 208, where the sampled produced fluids that were not used may be introduced into the storage container 208.

Although sampling of the produced fluid is described with reference to FIG. 2 from the sampling chamber 218, sampling of the produced fluid may also be taken from the storage container 208, without departing from the scope of the present disclosure. Moreover, sampling of the produced fluid may be at any other location along the main tubular 212, without departing from the scope of the present disclosure.

After an optimal surfactant or surfactant blend has been identified, the optimal surfactant or surfactant blend may be added to the produced fluid to form an oil-water separation morphological phase by adding the surfactant or surfactant in the appropriate amount to the storage container 208 comprising the produced fluid. In other embodiments, the surfactant blend may be applied to other storage containers comprising produced fluids that have not yet had their water and oil separated, such as in a tank, a barrel, and the like.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments herein include:

Embodiment A: A method comprising: producing a bulk fluid from a subterranean formation, the bulk fluid comprising at least water and a hydrocarbon; sampling a portion of the fluid, thereby forming at least one sampled fluid; determining constituent parameters of the sampled fluid using the hydrophilic-lipophilic deviation (HLD) model according to Equation A for an ionic surfactant composition and Equation B for a nonionic surfactant composition:

$$\text{HLD} = ln(S) - k*\text{EACN} + c_c - \alpha_T(T - 25^\circ\ C.) \qquad \text{Equation A,}$$

$$\text{HLD} = b(S) - k*\text{EACN} + c_{cn} - c_T(T - 25^\circ\ C.) \qquad \text{Equation B,}$$

where S is salinity of the sampled fluid; b is a salinity constant; EACN is equivalent alkane carbon number for the hydrocarbon in the sampled fluid; T is temperature of the sampled fluid; $c_c$ is characteristic curvature for the ionic surfactant composition; $c_{cn}$ is characteristic curvature for the nonionic surfactant composition; $\alpha_T$ is a surfactant temperature constant for the ionic surfactant composition; and $c_T$ is a surfactant temperature constant for the nonionic surfactant composition;

determining an optimal surfactant or optimal surfactant blend to achieve an oil-water separation morphological phase distribution of the sampled fluid according to Equation C:

$$W_1 \cdot \text{HLD}^2 + W_2(\rho - \overline{\rho})^2 + W_3(\mu - \overline{\mu})^2 + W_4 \cdot \text{cost} + W_5 \cdot \text{uncertainty} + W_6 \cdot \text{HSE} + W_7 \cdot \text{experiment\_cost} + W_8 \cdot \text{robustness} \qquad \text{Equation C,}$$

where W is a user defined weighting factor, $\rho$ is density of the surfactant, $\mu$ is viscosity of the surfactant, cost is combined material cost and supply chain cost of the optimal surfactant or the optimal surfactant blend, uncertainty is a non-negative parameter characterizing the dispersion of the values attributed to a measured quantity or a quantity derived from at least one measured quantity, HSE is a health, safety, and environmental impact value of the optimal surfactant or the optimal surfactant blend, experiment_cost represents the time and money spent determining a desired surfactant, and robustness represents the ability of a selected surfactant to withstand changes to the physical environment without changing the HLD.

Embodiment A may have one or more of the following additional elements in any combination:

Element A1: The method of Embodiment A, wherein the HLD in Equation C is determined by Equation D for ionic surfactant compositions and Equation E for nonionic surfactant compositions:

$$HLD = S\sum_{i=1}^{N} c_i \cdot b_i(S) - EACN \sum_{i=1}^{N} c_i \cdot k_i +$$
$$\sum_{i=1}^{N} c_i \cdot c_{c,i} + (T - 25°\text{ C.})\sum_{i=1}^{N} c_i \cdot \alpha_{T,i} + f(A),$$

Equation D $$HLD = S\sum_{i=1}^{N} c_i \cdot \ln(S_i) - EACN \sum_{i=1}^{N} c_i \cdot k_i +$$
$$\sum_{i=1}^{N} c_i \cdot c_{cn,i} + (T - 25°\text{ C.})\sum_{i=1}^{N} c_i \cdot c_{T,i} + f(A),$$

Equation E where $c_i$ is a composition of the optimal surfactant or an $i^{th}$ surfactant in the optimal surfactant blend.

Element A2: The method of Embodiment A, wherein the cost in Equation C is determined by:

$$\text{cost} = \Sigma_{i=1}^{N} c_i \cdot (\text{cost}_{m,i} + \text{cost}_{s,i}),$$

Equation F, where $\text{cost}_{m,i}$ is the material cost of the optimal surfactant or an $i^{th}$ surfactant in the optimal surfactant blend, and $\text{cost}_{s,i}$ is the supply chain cost of the optimal surfactant or the $i^{th}$ surfactant in the optimal surfactant blend.

Element A3: The method of Embodiment A and Element A2, wherein $\text{cost}_{s,i}$ is determined by:

$$\text{cost}_{s,i} = \text{cost}_{per\ sack} * n_{sack,i}$$

Equation G, where $\text{cost}_{per\ sack}$ is cost of the surfactant by sack of the optimal surfactant or the $i^{th}$ surfactant of the optimal surfactant blend, $n_{sack,i}$ is the number of sacks of the optimal surfactant or the $i^{th}$ surfactant of the optimal surfactant blend.

Element A4: The method of Embodiment A, wherein the uncertainty in Equation C is determined by:

$$\text{uncertainty} = \sum_{i=1}^{N} f_{un}(c_i, \text{uncertainty}_i),$$

Equation H where $f_{un}$ is a function of the uncertainty of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, uncertainty$_i$, of the optimal surfactant or of the $i^{th}$ surfactant of the optimal surfactant blend.

Element A5: The method of Embodiment A, wherein the uncertainty in Equation C is determined by Equation I for ionic surfactant compositions and Equation J for nonionic surfactant compositions:

$$\text{uncertainty}_{ionic} = S^2 \sum_{i=1}^{N} c_i^2 \cdot \sigma_{ln(S)} + EACN^2 \sum_{i=1}^{N} c_i^2 \cdot \sigma_{k_i} +$$
$$\sum_{i=1}^{N} c_i^2 \cdot \sigma_{c,i} + (T - 25°\text{ C.})^2 \sum_{i=1}^{N} c_i^2 \cdot \sigma_{\alpha_{T,i}},$$

Equation I $$\text{uncertainty}_{nonionic} = S^2 \sum_{i=1}^{N} c_i^2 \cdot \sigma_{b_i} + EACN^2 \sum_{i=1}^{N} c_i^2 \cdot \sigma_{k_i} +$$
$$\sum_{i=1}^{N} c_i^2 \cdot \sigma_{cn,i} + (T - 25°\text{ C.})^2 \sum_{i=1}^{N} c_i^2 \cdot \sigma_{c_{T,i}},$$

Equation J where $\sigma$ is a standard deviation, and $c_i$ is a composition of the optimal surfactant or an $i^{th}$ surfactant in the optimal surfactant blend.

Element A6: The method of Embodiment A, wherein the HSE in Equation C is determined by:

$$HSE = \sum_{i=1}^{N} g(c_i, HSE_i),$$

Equation K where g is a function of the HSE of the optimal surfactant or of the $i^{th}$ surfactant of the optimal surfactant blend, based on a composition, $c_i$, of the optimal surfactant or of the surfactant of the optimal surfactant blend, and the HSE, $HSE_i$, of the optimal surfactant or of the $i^{th}$ surfactant of the optimal surfactant blend.

Element A7: The method of Embodiment A, wherein the experiment_cost in Equation C is determined by:

$$\text{experiment\_cost} = \sum_{i=1}^{N} f_{exp}(c_i, \text{uncertainty}_i)$$

Equation L where $f_{exp}$ is a function of the experimental cost of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, uncertainty$_i$, of the optimal surfactant or of the $i^{th}$ surfactant of the optimal surfactant blend.

Element A8: The method of Embodiment A, wherein the experiment_cost in Equation C is determined by:

$$\text{robustness} = \sum_{i=1}^{N} f_{rb}(c_i, \text{uncertainty}_i, T, \sigma_T)$$

where $f_{rb}$ is a function of the robustness of the optimal surfactant or of the $i^{th}$ surfactant of the optimal surfactant blend, based on a composition, $c_i$, of the optimal surfactant or of the $i^{th}$ surfactant of the optimal surfactant blend, the uncertainty, uncertainty$_i$, of the optimal surfactant or of the $i^{th}$ surfactant of the optimal surfactant blend, the temperature, T, of the optimal surfactant or of the $i^{th}$ surfactant of the optimal surfactant blend, and a standard deviation of the temperature, $\sigma_T$, of the optimal surfactant or of the $i^{th}$ surfactant of the optimal surfactant blend.

By way of non-limiting example, exemplary combinations applicable to A include: combination of Elements A2 and A3; combination of Elements A1, A2, and A3; combination of Elements A4, A5, and A8, combination of Elements A2, A3, and A7, etc.

Embodiment B: A method comprising: producing a bulk fluid from a subterranean formation, the bulk fluid comprising at least water and a hydrocarbon; sampling a portion of the fluid, thereby forming at least one sampled fluid; determining constituent parameters of the sampled fluid using the hydrophilic-lipophilic deviation (HLD) model according to Equation A for an ionic surfactant composition and Equation B for a nonionic surfactant composition:

$$HLD = ln(S) - k*EACN + c_c - \alpha_T(T - 25°\text{ C.})$$

Equation A, $$HLD = b(S) - k*EACN + c_{cn} - c_T(T - 25°\text{ C.})$$

Equation B, where S is salinity of the sampled fluid; b is a salinity constant; EACN is equivalent alkane carbon number for the hydrocarbon in the sampled fluid; T is temperature of the sampled fluid; $c_c$ is characteristic curvature for the ionic surfactant composition; $c_{cn}$ is characteristic curvature for the nonionic surfactant composition; $\alpha_T$ is a surfactant temperature constant for the ionic surfactant composition; and $c_T$ is a surfactant temperature constant for the nonionic surfactant composition;

determining an optimal surfactant or optimal surfactant blend to achieve a first oil-water separation morphological phase distribution of the sampled fluid according to Equation C:

$$\min W_1 \cdot HLD^2 + W_2(\rho - \bar{\rho})^2 + W_3(\mu - \bar{\mu})^2 + W_4 \cdot \text{cost} + W_5 \cdot \text{uncertainty} + W_6 \cdot HSE + W_7 \cdot \text{experiment\_cost} + W_8 \cdot \text{robustness} \quad \text{Equation C,}$$

where W is a user defined weighting factor, ρ is density of the surfactant, μ is viscosity of the surfactant, cost is combined material cost and supply chain cost of the optimal surfactant or the optimal surfactant blend, uncertainty is a non-negative parameter characterizing the dispersion of the values attributed to a measured quantity or a quantity derived from at least one measured quantity, HSE is a health, safety, and environmental impact value of the optimal surfactant or the optimal surfactant blend, experiment_cost represents the time and money spent determining a desired surfactant, and robustness represents the ability of a selected surfactant to withstand changes to the physical environment without changing the HLD;

introducing the optimal surfactant or the optimal surfactant blend into the bulk fluid in an amount sufficient to achieve a second oil-water separation morphological phase distribution of the bulk fluid.

Embodiment B may have one or more of the following additional elements in any combination:

Element B1: The method of Embodiment B, wherein the HLD in Equation C is determined by Equation D for ionic surfactant compositions and Equation E for nonionic surfactant compositions:

$$HLD = S\sum_{i=1}^{D} c_i \cdot b_i(S) - EACN \sum_{i=1}^{N} c_i \cdot k_i + \sum_{i=1}^{N} c_i \cdot c_{c,i} + (T - 25°\text{C.})\sum_{i=1}^{N} c_i \cdot \alpha_{T,i} + f(A), \quad \text{Equation D}$$

$$HLD = S\sum_{i=1}^{N} c_i \cdot \ln(S_i) - EACN \sum_{i=1}^{N} c_i \cdot k_i + \sum_{i=1}^{N} c_i \cdot c_{cn,i} + (T - 25°\text{C.})\sum_{i=1}^{N} c_i \cdot c_{T,i} + f(A), \quad \text{Equation E}$$

where $c_i$ is a composition of the optimal surfactant or an $i^{th}$ surfactant in the optimal surfactant blend.

Element B2: The method of Embodiment B, wherein the cost in Equation C is determined by:

$$\text{cost} = \Sigma_{i=1}^{N} c_i \cdot (\text{cost}_{m,i} + \text{cost}_{s,i}), \quad \text{Equation F}$$

where $\text{cost}_{m,i}$ is the material cost of the optimal surfactant or an $i^{th}$ surfactant in the optimal surfactant blend, and $\text{cost}_{s,i}$ is the supply chain cost of the optimal surfactant or the $i^{th}$ surfactant in the optimal surfactant blend.

Element B3: The method of Embodiment B and Element B2, wherein $\text{cost}_{s,i}$ is determined by:

$$\text{cost}_{s,i} = \text{cost}_{per\ sack} * n_{sack,i} \quad \text{Equation G,}$$

where $\text{cost}_{m,i}$ is the material cost of the optimal surfactant or an $i^{th}$ surfactant in the optimal surfactant blend, and $\text{cost}_{s,i}$ is the supply chain cost of the optimal surfactant or the $i^{th}$ surfactant in the optimal surfactant blend.

Element B4: The method of Embodiment B, wherein the uncertainty in Equation C is determined by:

$$\text{uncertainty} = \sum_{i=1}^{N} f_{un}(c_i, \text{uncertainty}_i), \quad \text{Equation H}$$

where $f_{un}$ is a function of the uncertainty of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, $\text{uncertainty}_i$, of the optimal surfactant or of the $i^{th}$ surfactant of the optimal surfactant blend.

Element B5: The method of Embodiment B, wherein the uncertainty in Equation C is determined by Equation I for ionic surfactant compositions and Equation J for nonionic surfactant compositions:

$$\text{uncertainty}_{ionic} = S^2 \sum_{i=1}^{N} c_i^2 \cdot \sigma_{ln(S)} + EACN^2 \sum_{i=1}^{N} c_i^2 \cdot \sigma_{k_i} + \sum_{i=1}^{N} c_i^2 \cdot \sigma_{c,i} + (T - 25°\text{C.})^2 \sum_{i=1}^{N} c_i^2 \cdot \sigma_{\alpha_{T,i}}, \quad \text{Equation I}$$

$$\text{uncertainty}_{nonionic} = S^2 \sum_{i=1}^{N} c_i^2 \cdot \sigma_{b_i} + EACN^2 \sum_{i=1}^{N} c_i^2 \cdot \sigma_{k_i} + \sum_{i=1}^{N} c_i^2 \cdot \sigma_{cn,i} + (T - 25°\text{C.})^2 \sum_{i=1}^{N} c_i^2 \cdot \sigma_{c_{T,i}}, \quad \text{Equation J}$$

where σ is a standard deviation, and $c_i$ is a composition of the optimal surfactant or an $i^{th}$ surfactant in the optimal surfactant blend.

Element B6: The method of Embodiment B, wherein the HSE in Equation C is determined by:

$$HSE = \sum_{i=1}^{N} g(c_i, HSE_i), \quad \text{Equation K}$$

where g is a function of the HSE of the optimal surfactant or of the $i^{th}$ surfactant of the optimal surfactant blend, based on a composition, $c_i$, of the optimal surfactant or of the surfactant of the optimal surfactant blend, and the HSE, $HSE_i$, of the optimal surfactant or of the $i^{th}$ surfactant of the optimal surfactant blend.

Element B7: The method of Embodiment B, wherein the experiment_cost in Equation 3 is determined by:

$$\text{experiment\_cost} = \sum_{i=1}^{N} f_{exp}(c_i, \text{uncertainty}_i), \quad \text{Equation L}$$

where $f_{exp}$ is a function of the experimental cost of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, uncertainty$_i$, of the optimal surfactant or of the $i^{th}$ surfactant of the optimal surfactant blend.

Element B8: The method of Embodiment B, wherein the experiment_cost in Equation C is determined by:

$$\text{robustness} = \sum_{i=1}^{N} f_{rb}(c_i, \text{uncertainty}_i, T, \sigma_T)$$

where $f_{rb}$ is a function of the robustness of the optimal surfactant or of the $i^{th}$ surfactant of the optimal surfactant blend, based on a composition, $c_i$, of the optimal surfactant or of the $i^{th}$ surfactant of the optimal surfactant blend, the uncertainty, uncertainty$_i$, of the optimal surfactant or of the $i^{th}$ surfactant of the optimal surfactant blend, the temperature, T, of the optimal surfactant or of the $i^{th}$ surfactant of the optimal surfactant blend, and a standard deviation of the temperature, $\sigma_T$, of the optimal surfactant or of the $i^{th}$ surfactant of the optimal surfactant blend.

Element B9: The method of Embodiment B, further comprising separating water from hydrocarbon from the bulk fluid forming the second oil-water separation morphological phase distribution.

Element B10: The method of Embodiment B, wherein the wherein bulk fluid is retained in a storage container, and wherein the step of introducing the optimal surfactant or the optimal surfactant blend into the bulk fluid in an amount sufficient to achieve a second oil-water separation morphological phase distribution of the bulk fluid further comprises introducing the optimal surfactant or the optimal surfactant blend into the storage container.

By way of non-limiting example, exemplary combinations applicable to B include: combination of Elements B2 and B3; combination of Elements B1, B2, B3 and B8; combination of Elements B4, B5, and B10, combination of Elements B2, B3, and B7, etc.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:
1. A method comprising:
   producing a bulk fluid from a subterranean formation, the bulk produced fluid comprising at least water and a hydrocarbon;
   sampling a portion of the produced bulk fluid, thereby forming at least one sampled fluid;
   determining constituent parameters of the sampled fluid using a hydrophilic-lipophilic deviation (HLD) model according to Equation A for an ionic surfactant composition or Equation B for a nonionic surfactant composition:

$$HLD = ln(S) - k^* EACN + c_c - \alpha_T(T - 25° C.) \quad \text{Equation A,}$$

$$HLD = b(S) - k^* EACN + c_{cn} - c_T(T - 25° C.) \quad \text{Equation B,}$$

where S is salinity of the sampled fluid; b is a salinity constant; EACN is equivalent alkane carbon number for the hydrocarbon in the sampled fluid; T is temperature of the sampled fluid; $c_c$ is characteristic curvature for the ionic surfactant composition; $c_{cn}$ is characteristic curvature for the nonionic surfactant composition; $\alpha_T$ is a surfactant temperature constant for the ionic surfactant composition; and $c_T$ is a surfactant temperature constant for the nonionic surfactant composition;
   determining an optimal surfactant or optimal surfactant blend to achieve an oil-water separation morphological phase distribution of the sampled fluid according to Equation C:

$$\min \quad W_1 \cdot HLD^2 + W_2(\rho - \bar{\rho})^2 + W_3(\mu - \bar{\mu})^2 + W_4 \cdot \text{cost} + W_5 \cdot \text{uncertainty} + W_6 \cdot HSE + W_7 \cdot \text{experiment\_cost} + W_8 \cdot \text{robustness} \quad \text{Equation C,}$$

where W is a user defined weighting factor, $\rho$ is density of the optimal surfactant or the optimal surfactant blend, $\mu$ is viscosity of the optimal surfactant or the optimal surfactant blend, cost is combined material cost and transportation cost of the optimal surfactant or the optimal surfactant blend, HSE is a health, safety, and environmental risk rating value of the optimal surfactant or the optimal surfactant blend, experiment_cost represents the monetary cost of determining the properties of the ionic surfactant composition or nonionic surfactant composition according to Equation A or Equation B, robustness represents the ability of the optimal surfactant or surfactant blend to maintain steady HLD in a surrounding environment, and uncertainty is a non-negative parameter determined according to Equation D for an ionic optimal surfactant or ionic surfactant in the optimal surfactant blend or Equation E for a nonionic optimal surfactant or nonionic surfactant in the optimal surfactant blend:

$$\text{uncertainly}_{ionic} = S^2 \sum_{i=1}^{N} c_i^2 \cdot \sigma_{ln(S)} + EACN^2 \sum_{i=1}^{N} c_i^2 \cdot \sigma_{k_i} + \sum_{i=1}^{N} c_i^2 \cdot \sigma_{c,i} + (T - 25° \text{ C.})^2 \sum_{i=1}^{N} c_i^2 \cdot \sigma_{\alpha_{T,i}},$$

Equation D $$\text{uncertainly}_{nonionic} = S^2 \sum_{i=1}^{N} c_i^2 \cdot \sigma_{b_i} + EACN^2 \sum_{i=1}^{N} c_i^2 \cdot \sigma_{k_i} + \sum_{i=1}^{N} c_i^2 \cdot \sigma_{cn,i} + (T - 25° \text{ C.})^2 \sum_{i=1}^{N} c_i^2 \cdot \sigma_{c_{T,i}},$$

Equation E where σ is a standard deviation, and $c_i$ is a composition of the optimal surfactant or an $i^{th}$ surfactant in the optimal surfactant blend; and adding the optimal surfactant or surfactant blend to the produced bulk fluid to form an oil-water separation morphological phase of the produced bulk fluid.

2. The method of claim 1, wherein the HLD in Equation C is determined by Equation F for ionic surfactant compositions and Equation G for nonionic surfactant compositions:

$$HLD = S \sum_{i=1}^{N} c_i \cdot b_i(S) - EACN \sum_{i=1}^{N} c_i \cdot k_i + \sum_{i=1}^{N} c_i \cdot c_{c,i} + (T - 25° \text{ C.}) \sum_{i=1}^{N} c_i \cdot \alpha_{T,i} + f(A),$$

Equation F $$HLD = S \sum_{i=1}^{N} c_i \cdot \ln(S_i) - EACN \sum_{i=1}^{N} c_i \cdot k_i + \sum_{i=1}^{N} c_i \cdot c_{cn,i} + (T - 25° \text{ C.}) \sum_{i=1}^{N} c_i \cdot c_{T,i} + f(A),$$

Equation G where $C_i$ is a composition of the optimal surfactant or an $i^{th}$ surfactant in the optimal surfactant blend.

3. The method of claim 1, wherein the cost in Equation C is determined by:

cost=$\Sigma_{i=1}^{N} c_i \cdot (\text{cost}_{m,i} + \text{cost}_{s,i})$, where $\text{cost}_{m,i}$ is the material cost of the optimal surfactant or an $i^{th}$ surfactant in the optimal surfactant blend, and $\text{cost}_{s,i}$ is the transportation cost of the optimal surfactant or the $i^{th}$ surfactant in the optimal surfactant blend.

4. The method of claim 3, wherein $\text{cost}_{s,i}$ is determined by:

$\text{cost}_{s,i} = \text{cost}_{per\ sack} * n_{sack,i}$ where $\text{cost}_{per\ sack}$ is material cost of the by sack of the optimal surfactant or the $i^{th}$ surfactant of the optimal surfactant blend, $n_{sack,i}$ is the number of sacks of the optimal surfactant or the $i^{th}$ surfactant of the optimal surfactant blend.

5. The method of claim 1, wherein the HSE in Equation C is determined by:

$$HSE = \sum_{i=1}^{N} g(c_i, HSE_i),$$

where g is a function of the HSE of the optimal surfactant or of the $i^{th}$ surfactant of the optimal surfactant blend, based on a composition, $c_i$, of the optimal surfactant or of the $i^{th}$ surfactant of the optimal surfactant blend, and the HSE risk rating value, $HSE_i$, of the optimal surfactant or of the $i^{th}$ surfactant of the optimal surfactant blend.

6. The method of claim 1, wherein the experiment_cost in Equation C is determined by:

$$\text{experiment\_cost} = \sum_{i=1}^{N} f_{exp}(c_i, \text{uncertainty}_i),$$

where $f_{exp}$ is a function of the experimental cost of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, uncertainty$_i$, of the optimal surfactant or of the $i^{th}$ surfactant of the optimal surfactant blend.

7. The method of claim 1, wherein the experiment_cost in Equation C is determined by:

$$\text{robustness} = \sum_{i=1}^{N} f_{rb}(c_i, \text{uncertainty}_i, T, \sigma_T),$$

where $f_{rb}$ is a function of the robustness of the optimal surfactant or of the $i^{th}$ surfactant of the optimal surfactant blend, based on a composition, $c_i$, of the optimal surfactant or of the $i^{th}$ surfactant of the optimal surfactant blend, the uncertainty, uncertainty$_i$, of the optimal surfactant or of the $i^{th}$ surfactant of the optimal surfactant blend, the temperature, T, of the optimal surfactant or of the $i^{th}$ surfactant of the optimal surfactant blend, and a standard deviation of the temperature, $\rho_T$, of the optimal surfactant or of the $i^{th}$ surfactant of the optimal surfactant blend.

8. A method comprising:

producing a bulk fluid from a subterranean formation, the produced bulk fluid comprising at least water and a hydrocarbon;

sampling a portion of the produced bulk fluid, thereby forming at least one sampled fluid;

determining constituent parameters of the sampled fluid using a hydrophilic-lipophilic deviation (HLD) model according to Equation A for an ionic surfactant composition or Equation B for a nonionic surfactant composition:

HLD=$ln(S)-k*$EACN+$c_c-\alpha_T(T-25°$ C.)   Equation A,

HLD=$b(S)-k*$EACN+$c_{cn}-c_T(T-25°$ C.)   Equation B, where S is salinity of the sampled fluid; b is a salinity constant; EACN is equivalent alkane carbon number for the hydrocarbon in the sampled fluid; T is temperature of the sampled fluid; $c_c$ is characteristic curvature for the ionic surfactant composition; $c_{cn}$ is characteristic curvature for the nonionic surfactant composition; $\alpha_T$ is a surfactant temperature constant for the ionic surfactant composition; and $c_T$ is a surfactant temperature constant for the nonionic surfactant composition;

determining an optimal surfactant or optimal surfactant blend to achieve a first oil-water separation morphological phase distribution of the sampled fluid according to Equation C:

$$\min W_1 \cdot HLD^2 + W_2(\rho - \bar{\rho})^2 + W_3(\mu - \bar{\mu})^2 + W_4 \cdot \text{cost} + W_5 \cdot \text{uncertainty} + W_6 \cdot HSE + W_7 \cdot \text{experiment\_cost} + W_8 \cdot \text{robustness} \quad \text{Equation C},$$

where W is a user defined weighting factor, $\rho$ is density of the optimal surfactant or the optimal surfactant blend, $\mu$ is viscosity of the optimal surfactant or the optimal surfactant blend, cost is combined material cost and transportation cost of the optimal surfactant or the optimal surfactant blend, HSE is a health, safety, and environmental risk rating value of the optimal surfactant or the optimal surfactant blend, experiment_cost represents the monetary cost of determining the properties of the ionic surfactant composition or nonionic surfactant composition according to Equation A or Equation B, robustness represents the ability of the optimal surfactant or surfactant blend to maintain steady HLD in a surrounding environment, and uncertainty is a nonnegative parameter determined according to Equation D for an ionic optimal surfactant or ionic surfactant in the optimal surfactant blend or Equation E for a nonionic optimal surfactant or nonionic surfactant in the optimal surfactant blend:

$$\text{uncertainly}_{ionic} = S^2 \sum_{i=1}^{N} c_i^2 \cdot \sigma_{ln(S)} + EACN^2 \sum_{i=1}^{N} c_i^2 \cdot \sigma_{k_i} + \sum_{i=1}^{N} c_i^2 \cdot \sigma_{c,i} + (T - 25^\circ \text{C.})^2 \sum_{i=1}^{N} c_i^2 \cdot \sigma_{\alpha_{T,i}}, \quad \text{Equation D}$$

$$\text{uncertainly}_{nonionc} = S^2 \sum_{i=1}^{N} c_i^2 \cdot \sigma_{b_i} + EACN^2 \sum_{i=1}^{N} c_i^2 \cdot \sigma_{k_i} + \sum_{i=1}^{N} c_i^2 \cdot \sigma_{cn,i} + (T - 25^\circ \text{C.})^2 \sum_{i=1}^{N} c_i^2 \cdot \sigma_{c_{T,i}}, \quad \text{Equation E}$$

where $\sigma$ is a standard deviation, and $c_i$ is a composition of the optimal surfactant or an $i^{th}$ surfactant in the optimal surfactant blend;

introducing the optimal surfactant or the optimal surfactant blend into the produced bulk fluid in an amount sufficient to achieve a second oil-water separation morphological phase distribution of the produced bulk fluid.

9. The method of claim 8, wherein the HLD in Equation C is determined by Equation F for ionic surfactant compositions and Equation G for nonionic surfactant compositions:

$$HLD = S \sum_{i=1}^{N} c_i \cdot b_i(S) - EACN \sum_{i=1}^{N} c_i \cdot k_i + \sum_{i=1}^{N} c_i \cdot c_{c,i} + (T - 25^\circ \text{C.}) \sum_{i=1}^{N} c_i \cdot \alpha_{T,i} + f(A), \quad \text{Equation F}$$

$$HLD = S \sum_{i=1}^{N} c_i \cdot \ln(S_i) - EACN \sum_{i=1}^{N} c_i \cdot k_i + \sum_{i=1}^{N} c_i \cdot c_{cn,i} + (T - 25^\circ \text{C.}) \sum_{i=1}^{N} c_i \cdot c_{T,i} + f(A), \quad \text{Equation G}$$

where $c_i$ is a composition of the optimal surfactant or an $i^{th}$ surfactant in the optimal surfactant blend.

10. The method of claim 8, wherein the cost in Equation C is determined by:

$$\text{cost} = \Sigma_{i=1}^{N} c_i \cdot (\text{cost}_{m,i} + \text{cost}_{s,i}),$$

where $\text{cost}_{m,i}$ is the material cost of the optimal surfactant or an $i^{th}$ surfactant in the optimal surfactant blend, and $\text{cost}_{s,i}$ is the transportation cost of the optimal surfactant or the $i^{th}$ surfactant in the optimal surfactant blend.

11. The method of claim 10, wherein $\text{cost}_{s,i}$ is determined by:

$$\text{cost}_{s,i} = \text{cost}_{per\ sack} * n_{sack,i},$$

where $\text{cost}_{m,i}$ is the material cost of the optimal surfactant or an $i^{th}$ surfactant in the optimal surfactant blend, and $\text{cost}_{s,i}$ is the transportation cost of the optimal surfactant or the $i^{th}$ surfactant in the optimal surfactant blend.

12. The method of claim 8, wherein the HSE in Equation C is determined by:

$$HSE = \sum_{i=1}^{N} g(c_i, HSE_i),$$

where g is a function of the HSE of the optimal surfactant or of the $i^{th}$ surfactant of the optimal surfactant blend, based on a composition, $c_i$, of the optimal surfactant or of the $i^{th}$ surfactant of the optimal surfactant blend, and the HSE, $HSE_i$, of the optimal surfactant or of the $i^{th}$ surfactant of the optimal surfactant blend.

13. The method of claim 8, wherein the experiment_cost in Equation C is determined by:

$$\text{experiment\_cost} = \sum_{i=1}^{N} f_{exp}(c_i, \text{uncertainty}_i),$$

where $f_{exp}$ is a function of the experimental cost of the optimal surfactant or of the $i^{th}$ surfactant of the optimal surfactant blend, based on a composition, $c_i$, of the optimal surfactant or of the $i^{th}$ surfactant of the optimal surfactant blend, and the uncertainty, $\text{uncertainty}_i$, of the optimal surfactant or of the $i^{th}$ surfactant of the optimal surfactant blend.

14. The method of claim 8, wherein the experiment_cost in Equation C is determined by:

$$\text{robustness} = \sum_{i=1}^{N} f_{rb}(c_i, \text{uncertainty}_i, T, \sigma_T),$$

where $f_{r,b}$ is a function of the robustness of the optimal surfactant or of the $i^{th}$ surfactant of the optimal surfactant blend, based on a composition, $c_i$, of the optimal surfactant or of the $i^{th}$ surfactant of the optimal surfactant blend, the uncertainty, $\text{uncertainty}_i$, of the optimal surfactant or of the $i^{th}$ surfactant of the optimal surfactant blend, the temperature, T, of the optimal surfactant or of the $i^{th}$ surfactant of the optimal surfactant blend, and a standard deviation of the temperature, $\sigma_T$, of the optimal surfactant or of the $i^{th}$ surfactant of the optimal surfactant blend.

15. The method of claim 8, further comprising separating water from hydrocarbon from the produced bulk fluid forming the second oil-water separation morphological phase distribution.

16. The method of claim 8, wherein the produced bulk fluid is retained in a storage container, and wherein the step of introducing the optimal surfactant or the optimal surfactant blend into the produced bulk fluid in an amount sufficient to achieve a second oil-water separation morphological phase distribution of the produced bulk fluid further comprises introducing the optimal surfactant or the optimal surfactant blend into the storage container.

\* \* \* \* \*

UNITED STATES PATENT AND TRADEMARK OFFICE
CERTIFICATE OF CORRECTION

PATENT NO.         : 9,657,565 B2                                    Page 1 of 1
APPLICATION NO.    : 14/889091
DATED              : May 23, 2017
INVENTOR(S)        : Sanja Natali et al.

It is certified that error appears in the above-identified patent and that said Letters Patent is hereby corrected as shown below:

In the Claims

In Column 20, Line 38:
Replace "temperature, $\rho_T$," with -- temperature, $\sigma_T$, --.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*